(12) United States Patent
Kwon et al.

(10) Patent No.: US 11,478,157 B2
(45) Date of Patent: Oct. 25, 2022

(54) APPARATUS AND METHOD FOR ESTIMATING BIO-INFORMATION

(71) Applicant: SAMSUNG ELECTRONICS CO., LTD., Suwon-si (KR)

(72) Inventors: Yong Joo Kwon, Yongin-si (KR); Jae Min Kang, Seoul (KR); Sang Yun Park, Hwaseong-si (KR); Youn Ho Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 794 days.

(21) Appl. No.: 16/407,729

(22) Filed: May 9, 2019

(65) Prior Publication Data
US 2020/0093377 A1 Mar. 26, 2020

(30) Foreign Application Priority Data

Sep. 21, 2018 (KR) ........................ 10-2018-0114185

(51) Int. Cl.
| | | |
|---|---|---|
| *A61B 5/0205* | (2006.01) | |
| *A61B 5/00* | (2006.01) | |
| *A61B 5/02* | (2006.01) | |
| *A61B 5/021* | (2006.01) | |
| *A61B 5/024* | (2006.01) | |
| *A61B 5/16* | (2006.01) | |

(52) U.S. Cl.
CPC ............ *A61B 5/0205* (2013.01); *A61B 5/681* (2013.01); *A61B 5/6898* (2013.01); *A61B 5/7278* (2013.01); *A61B 5/021* (2013.01); *A61B 5/02007* (2013.01); *A61B 5/02433* (2013.01); *A61B 5/165* (2013.01); *A61B 5/442* (2013.01); *A61B 5/6843* (2013.01); *A61B 2560/0223* (2013.01); *A61B 2562/0238* (2013.01); *A61B 2562/0252* (2013.01); *A61B 2562/12* (2013.01)

(58) Field of Classification Search
None
See application file for complete search history.

(56) References Cited

U.S. PATENT DOCUMENTS

| | | |
|---|---|---|
| 2015/0351675 A1 | 12/2015 | Cheng |
| 2016/0113530 A1 | 4/2016 | Nagahiro et al. |

(Continued)

FOREIGN PATENT DOCUMENTS

| | | |
|---|---|---|
| JP | 3843576 B2 | 11/2006 |
| JP | 2016-152918 A | 8/2016 |

(Continued)

OTHER PUBLICATIONS

Communication dated May 18, 2020, issued by the European Patent Office in counterpart European Application No. 19187752.1.

(Continued)

*Primary Examiner* — Jay B Shah
(74) *Attorney, Agent, or Firm* — Sughrue Mion, PLLC

(57) ABSTRACT

Disclosed is an apparatus for estimating bio-information. The apparatus for estimating bio-information includes: a sensor part comprising a pulse wave sensor array configured to detect a pulse wave signal when an object contacts a contact surface of the sensor part, and a load sensor configured to detect a first contact load applied by the object to the contact surface; and a processor configured to obtain contact load distribution of the contact surface based on the pulse wave signal, and to estimate bio-information based on the contact load distribution.

26 Claims, 16 Drawing Sheets

(56) References Cited

U.S. PATENT DOCUMENTS

| | | |
|---|---|---|
| 2017/0014040 A1 | 1/2017 | Shim et al. |
| 2017/0095168 A1 | 4/2017 | Kwon et al. |
| 2017/0251935 A1 | 9/2017 | Yuen |
| 2018/0092602 A1 | 4/2018 | Hall et al. |
| 2018/0110427 A1 | 4/2018 | Kang et al. |
| 2018/0177413 A1 | 6/2018 | Kwon et al. |
| 2019/0046050 A1 | 2/2019 | Kato et al. |
| 2020/0085320 A1 | 3/2020 | Kwon et al. |

FOREIGN PATENT DOCUMENTS

| | | |
|---|---|---|
| JP | 2017-415 A | 1/2017 |
| KR | 10-2020-0032320 A | 3/2020 |
| WO | 2017/188092 A1 | 11/2017 |

OTHER PUBLICATIONS

Communication dated May 13, 2022 by the European Patent Office for European Patent Application No. 22150849.2.

APPARATUS AND METHOD FOR ESTIMATING BIO-INFORMATION

CROSS-REFERENCE TO RELATED APPLICATION(S)

This application claims priority from Korean Patent Application No. 10-2018-0114185, filed on Sep. 21, 2018, in the Korean Intellectual Property Office, the disclosure of which is incorporated herein by reference in its entirety.

BACKGROUND

1. Field

The following description relates to an apparatus and method for estimating bio-information in a non-invasive manner.

2. Description of the Related Art

As a method of measuring blood pressure in a non-invasive manner without damaging and causing pain to a human body, there is a cuff-based measurement method for measuring blood pressure using cuff pressure measurements and a cuffless measurement method for estimating blood pressure using pulse wave measurements without a cuff.

As the cuff-based measurement method for measuring blood pressure, there is a Korotkoff-sound method which measures blood pressure by winding a cuff around an upper arm and hearing the sound of blood vessels through a stethoscope during inflation and deflation of the cuff; and an Oscillometric method which measures blood pressure by winding a cuff around an upper arm and continuously measuring cuff pressure while inflating and then gradually deflating the cuff using an automated device, and measuring blood pressure based on a point of maximum pressure signal change.

As the cuffless measurement method for measuring blood pressure, there is a method of estimating blood pressure by calculating a Pulse Transit Time (PTT), and a Pulse Wave Analysis (PWA) method of estimating blood pressure by analyzing a pulse wave form.

SUMMARY

According to an aspect of an embodiment, there is provided an apparatus for estimating bio-information, including a sensor part and a processor. The sensor part may include: a pulse wave sensor array configured to detect a pulse wave signal when an object contacts a contact surface of the sensor part; and a load sensor configured to detect a first contact load applied by the object to the contact surface. The processor may be configured to obtain contact load distribution of the contact surface based on the pulse wave signal, obtain a second contact load at each position of the contact surface based on the contact load distribution and the first contact load, and estimate bio-information based on the second contact load and the pulse wave signal.

The pulse wave sensor array may include: a light source array configured to emit light onto the object; and a detector array configured to detect light reflected or scattered from the object.

The sensor part may further include a substrate on which the pulse wave sensor array may be formed in a predetermined pattern, by using at least one of wire bonding, flip-chip bonding, and a microfabrication technique.

The light source array may be arranged on the substrate by at least one of the wire bonding and the flip-chip bonding; and the detector array may be patterned on the substrate by the microfabrication technique.

The sensor part may further include a touch sensor disposed on the pulse wave sensor array to be contacted by the object.

The processor may be further configured to extract each direct current (DC) component from the pulse wave signal detected by the pulse wave sensor array at each position of the contact surface, and obtain a relative magnitude of the first contact load at each position based on the extracted each DC component.

The processor may be further configured to perform interpolation on the extracted each DC component to estimate the DC component at a specific position of the contact surface, in response to the pulse wave signal not being detected from the specific position of the contact surface.

The processor may be further configured to obtain the second contact load at each position by multiplying a value, obtained by dividing the first contact load by a total sum of the contact load distributions, by the relative magnitude of the contact load at each position.

The processor may be further configured to obtain a contact pressure between the object and the sensor part based on the second contact load of a region of interest and an area of the region of interest, and estimate the bio-information based on the contact pressure and the pulse wave signal.

The processor may be further configured to set the region of interest based on at least one of a blood vessel distribution of the object, an arrangement of the pulse wave sensor array, a specific position of the contact surface, and the second contact load at each position of the contact surface.

The processor may be further configured to obtain an oscillometric envelope which represents a contact pressure versus pulse wave signal amplitude at each measurement time, and estimate the bio-information based on the oscillometric envelope.

The processor may be further configured to estimate the bio-information based on a feature value of the oscillometric envelope, and the feature value may include one or more of a contact pressure value of a maximum amplitude point, a first contact pressure value that is less than the contact pressure value of the maximum amplitude point and having a first predetermined ratio to the contact pressure value of the maximum amplitude point, and a second contact pressure value that is greater than the contact pressure value of the maximum amplitude point and having a second predetermined ratio to the contact pressure value of the maximum amplitude point.

The apparatus may further include an output interface, which in response to a request for estimating bio-information, outputs guide information on contact pressure between the object and the sensor part.

The processor may be further configured to obtain a contact pressure of a region of interest based on the second contact load of the region of interest and an area of the region of interest, and determine a contact state between the object and the sensor part based on the contact pressure.

The bio-information may include one or more of blood pressure, vascular age, arterial stiffness, aortic pressure waveform, vascular compliance, stress index, degree of fatigue, skin elasticity, and skin age.

According to an aspect of another embodiment, there is provided a method of estimating bio-information, including: detecting a pulse wave signal when an object contacts a contact surface of a sensor; detecting a first contact load applied by the object to the contact surface; obtaining contact load distribution of the contact surface based on the pulse wave signal; obtaining a second contact load at each position of the contact surface based on the contact load distribution and the first contact load; and estimating bio-information based on the second contact load and the pulse wave signal.

The obtaining the contact load distribution may include: extracting each direct current (DC) component from the pulse wave signal at each position of the contact surface; and obtaining a relative magnitude of the first contact load at each position based on the extracted each DC component.

The obtaining the contact load distribution may include performing interpolation on the extracted each DC component to estimate the DC component at a specific position of the contact surface, in response to the pulse wave signal not being detected from the specific position of the contact surface.

The estimating the bio-information may include setting a region of interest based on at least one of a blood vessel distribution of the object, an arrangement of a pulse wave sensor array that detects the pulse wave signal, a specific position of the contact surface of the sensor, and the second contact load at each position of the contact surface.

The estimating the bio-information may further include obtaining a contact pressure between the object and the sensor based on the second contact load of a region of interest and an area of the region of interest.

The estimating the bio-information may include obtaining an oscillometric envelope which represents a contact pressure versus pulse wave signal amplitude at each measurement time, and estimating bio-information based on the oscillometric envelope.

According to an aspect of another embodiment, there is provided an apparatus for estimating bio-information, the apparatus including: a sensor part including a pulse wave sensor array configured to detect a pulse wave signal when an object contacts a contact surface of the sensor part, and a load sensor configured to detect a first contact load applied by the object to the contact surface; a memory configured to store a calibration model based on a reference pulse wave signal detected from a reference object; and a processor configured to: retrieve the calibration model from the memory; calibrate the pulse wave signal detected by the pulse wave sensor array, based on the calibration model; obtain a second contact load at each position of the contact surface based on the calibrated pulse wave signal and the first contact load; and estimate bio-information based on the second contact load and the calibrated pulse wave signal.

The reference object may include a reflecting panel that is made of a total reflection material and has a flat surface.

The processor may be further configured to generate the calibration model to calibrate a difference between output values of the pulse wave sensor array at each position of the contact surface, to 0, and store the calibration model in the memory.

The processor may be further configured to obtain a contact pressure based on the second contact load of a region of interest and an area of the region of interest, and estimate the bio-information based on the contact pressure and the calibrated pulse wave signal.

The object may be a user of the apparatus, and the processor may be further configured to determine whether to perform an additional calibration based on a result of estimating the bio-information based on the second contact load and the calibrated pulse wave signal, and provide guide information on the additional calibration to the user.

BRIEF DESCRIPTION OF THE DRAWINGS

The above and/or other aspects will be more apparent by describing certain example embodiments, with reference to the accompanying drawings, in which.

DETAILED DESCRIPTION

Figure 1A:
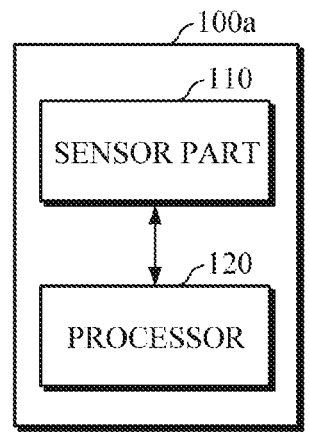
FIGS. 1A and 1B are block diagrams illustrating an apparatus for estimating bio-information according to embodiments.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, embodiments of an apparatus and method for estimating bio-information will be described in detail with reference to the accompanying drawings. Various embodiments of the apparatus for estimating bio-information, which will be described below, may be embedded in various devices such as a portable wearable device, a smart device, and the like. In this case, examples of the various devices may include, but are not limited to, a wearable device of various types such as a smart watch worn on the wrist, a smart band-type wearable device, a headphone-type wearable device, a hairband-type wearable device, and the like, a mobile device such as a smartphone, a tablet PC, and the like.

Figure 1B:
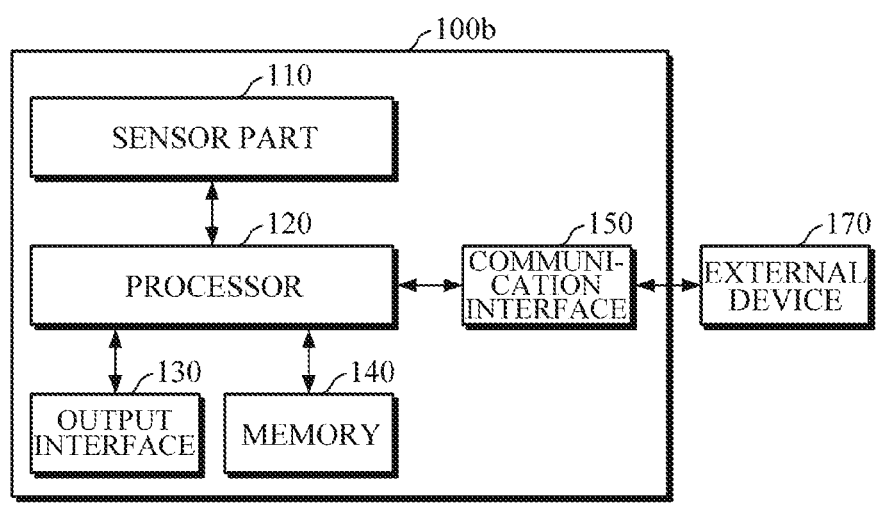
Figure 2A:
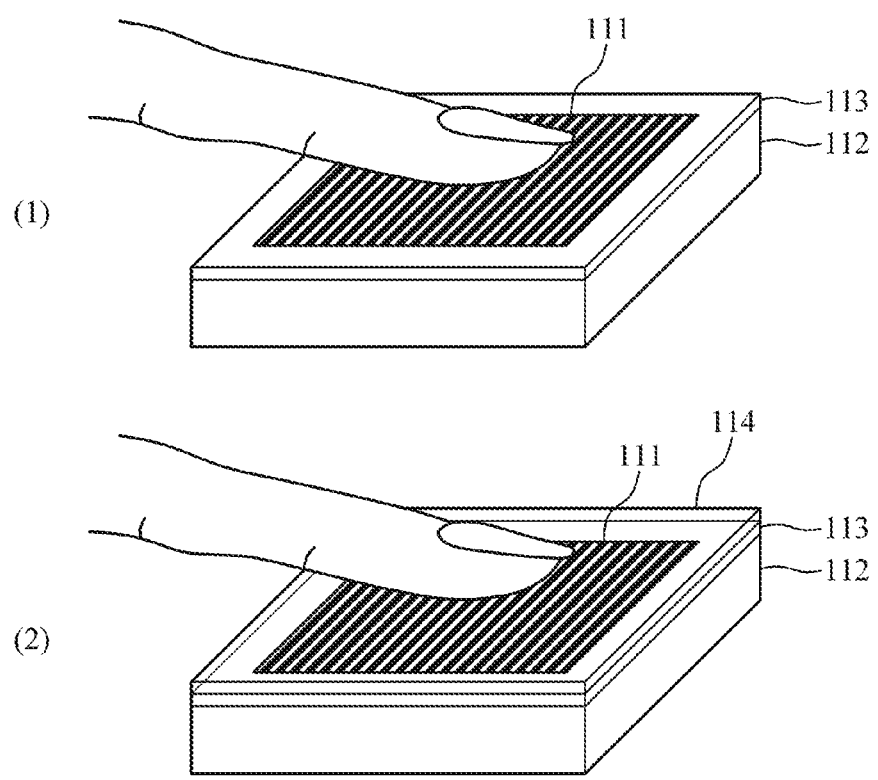
FIGS. 2A, 2B, and 2C are diagrams explaining structures of a sensor part of an apparatus for estimating bio-information according to embodiments.
Figure 2B:
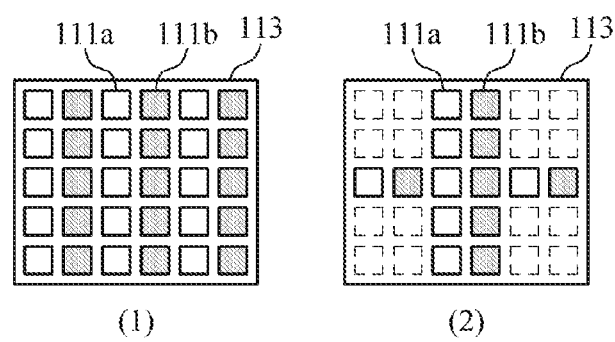
Figure 2C:
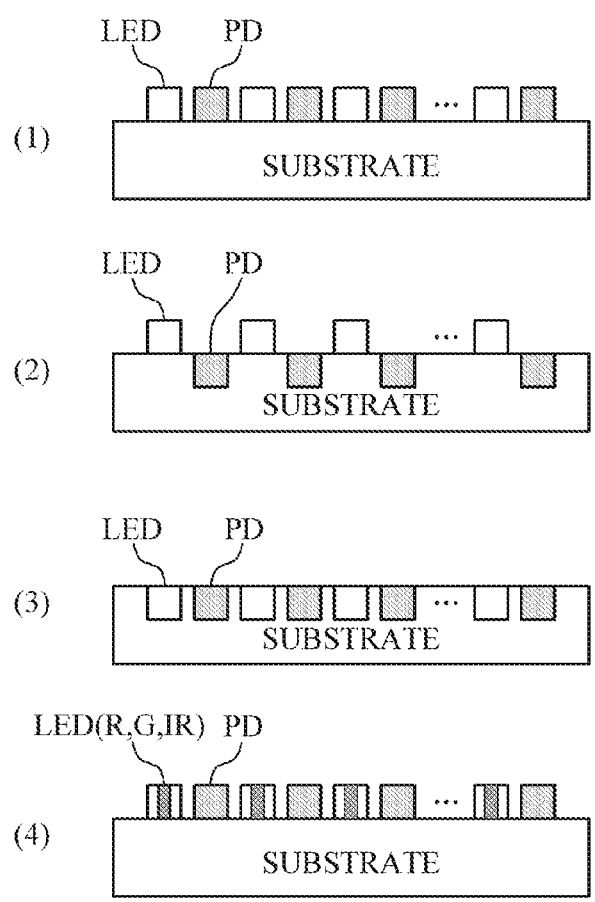

FIGS. 1A and 1B are block diagrams illustrating an apparatus for estimating bio-information according to embodiments. FIGS. 2A to 2C are diagrams explaining structures of a sensor part of an apparatus for estimating bio-information according to embodiments Referring to FIGS. 1A and 1B, the apparatuses 100a and 100b for estimating bio-information include a sensor part 110 and a processor 120.

The sensor part 110 includes: a pulse wave sensor array configured to detect a pulse wave signal at each position of a contact surface in response to contact of an object with the contact surface; and a load sensor configured to detect a first contact load applied by the object to the contact surface.

Referring to FIG. 2A, the sensor part 110 may further include a substrate 113. A plurality of pulse wave sensors may be arranged in a predetermined pattern on the substrate 113 to form the pulse wave sensor array 111. In the sensor part 110, the pulse wave sensor array 111 and the load sensor 112 may be formed in a multi-layer structure. Referring to (1) of FIG. 2A, the pulse wave sensor array 111 is formed at the top of the substrate 113, and the load sensor 112 may be disposed below the pulse wave sensor array 111. Referring to (2) of FIG. 2A, the sensor part 110 may further include a touch sensor 114 that is disposed on the top of the substrate 113 and configured to detect a touch made by an object. The pulse wave sensor array 111 may be formed on the touch sensor 114. The touch sensor 114 may be a capacitive-type sensor or an optical sensor, and may include a fingerprint sensor. The touch sensor 114 may be disposed at the top of the sensor part 110, such that in response to contact of the object, the touch sensor 114 may transmit information of a contact area of the object to the processor 120.

The pulse wave sensor array 111 includes: an array of light sources 111a which emit light onto an object, and an array of detectors 111b which detect light scattered or reflected from the object. In this case, a pair of the light source 111a and the detector 111b may form a pulse wave sensor. The light source 111a may include one or more light-emitting diodes (LED), laser diodes (LD), fluorescent bodies, and the like, but is not limited thereto. Further, the detector 111b may include a photo diode, a photo transistor (PTr), an image sensor (e.g., CMOS or CIS image sensor), and the like, but is not limited thereto.

The pulse wave sensor array 111 may be arranged in various patterns on the substrate 113. Referring to (1) of FIG. 2B, the pulse wave sensor array 111 includes a plurality of pulse wave sensors which are arranged in a square shape (e.g., a two-dimensional N×M matrix, wherein N and M denote positive integers). Referring to (2) of FIG. 2B, the plurality of pulse wave sensors may be arranged in a cross shape. However, the arrangement of the pulse wave sensor array 111 is not limited thereto, and the pulse wave sensor array 111 may be arranged in a circular shape, an oval shape, or various other shapes according to characteristics of an object. The light source array included in the pulse wave sensor array 111 may be driven either simultaneously or sequentially.

The array of light sources and the array of detectors, which are included in the pulse wave sensor array 111, may be formed on the substrate 113 by various methods.

For example, referring to (1) of FIG. 2C, the array of light sources (LED) and the array of detectors (PD) may be mounted on the substrate 113 by wire bonding or flip-chip bonding. As shown in (1) of FIG. 2C, the LEDs and PDs may be alternately disposed on the substrate 113, and both the LEDs and PDs may be protruded from the substrate 113. In another example, referring to (2) of FIG. 2C, the array of light sources (LED) may be mounted on the substrate 113 by wire bonding or flip-chip bonding; and the array of detectors (PD) may be patterned on the substrate 113 by microfabrication techniques. As shown in (2) of FIG. 2C, the LEDs may be produced from the substrate 113, and alternately disposed with the PDs that are patterned on the substrate 113. In this case, the substrate 113 may be a silicon substrate, but is not limited thereto. In another example, referring to (3) of FIG. 2C, the array of light sources (LED) and the array of detectors (PD) may be patterned on the substrate 113 by microfabrication techniques. As shown in (3) of FIG. 2C, the LEDs and the PDs may be alternately disposed on the substrate 113. In this case, the substrate 113 may be a silicon substrate, but is not limited thereto. Referring to (4) of FIG. 2C, each of the light sources may be formed as a plurality of LEDs to emit light of different wavelengths (e.g., red, green, and infrared wavelengths).

The processor 120 may be electrically connected to the sensor part 110, and may control the sensor part 110 in response to a request for estimating bio-information. The processor 120 may receive the pulse wave signal and the first contact load which are detected by the sensor part 110, and may estimate bio-information based on the received pulse wave signal and first contact load. In this case, the bio-information may include one or more of blood pressure, vascular age, arterial stiffness, aortic pressure waveform, vascular compliance, stress index, degree of fatigue, skin elasticity, and skin age, but is not limited thereto.

Figure 3A:
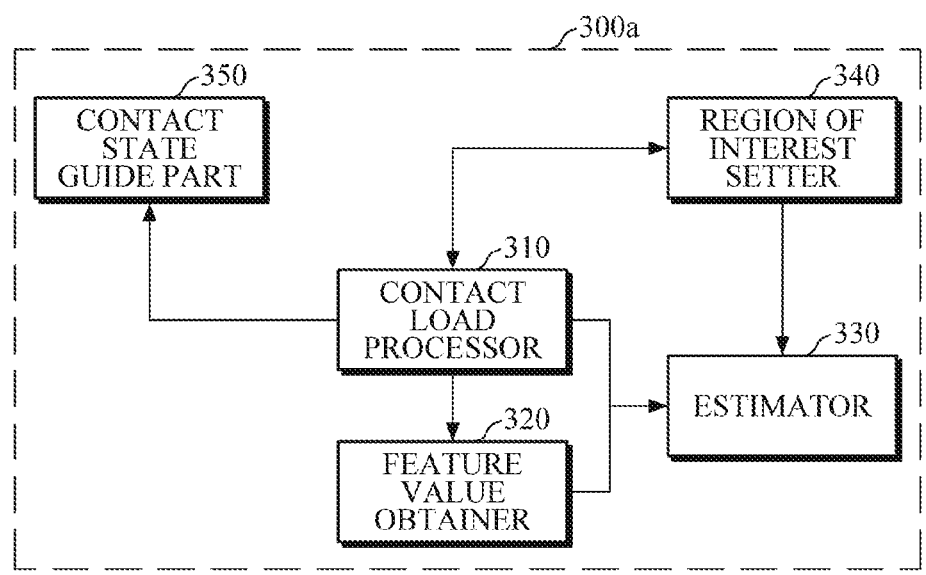
FIGS. 3A and 3B are block diagrams illustrating a processor according to embodiments.
Figure 3B:
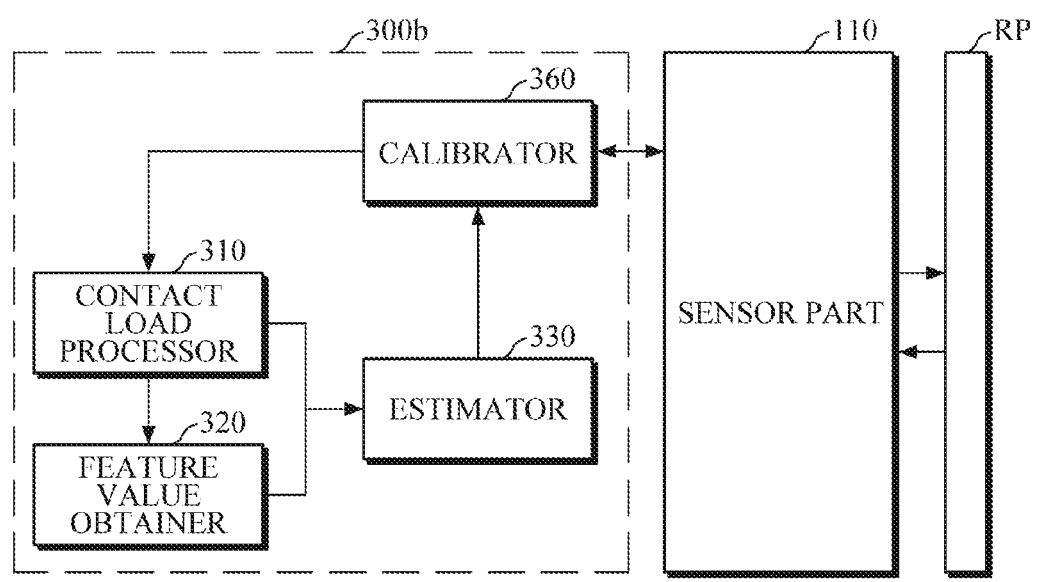

FIGS. 3A and 3B are block diagrams illustrating a processor according to embodiments of the present disclosure. FIGS. 4A to 4E are diagrams explaining an example of estimating bio-information using oscillometry. By referring to FIGS. 1A to 4E, embodiments of processors 300a and 300b will be described below.

Referring to FIG. 3A, the processor 300a according to an embodiment of the present disclosure includes a contact load processor 310, a feature value obtainer 320, an estimator 330, a region of interest setter 340, and a contact state guide part 350.

Figure 4A:
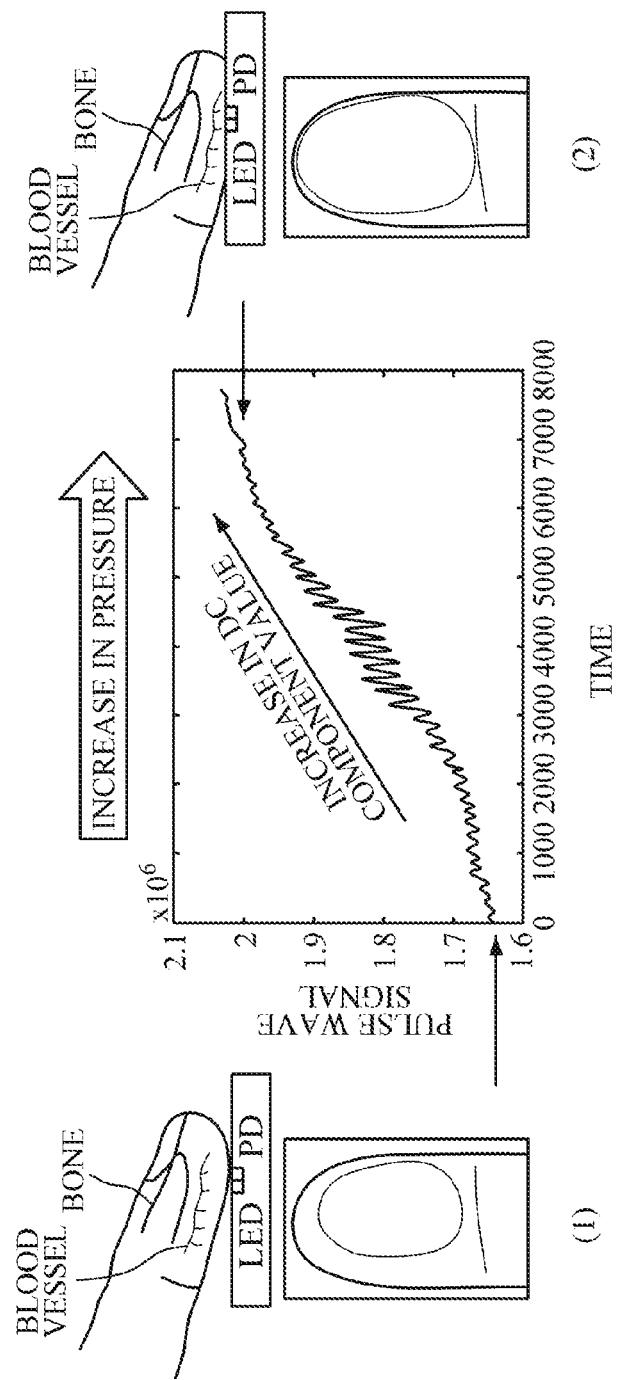
FIGS. 4A, 4B, 4C, 4D, and 4E are diagrams explaining an example of estimating bio-information using oscillometry.

The contact load processor 310 may obtain contact load distribution of a contact surface of the sensor part 110 by using a pulse wave signal detected by the pulse wave sensor array 111 at each position of the contact surface. Referring to FIG. 4A, while a user contacts the contact surface of the sensor part 110 with a finger as illustrated in (1) of FIG. 4A, when the finger presses the contact surface of the sensor part 110 with gradually increasing force to reach a state as illustrated in (2) of FIG. 4A, blood flows out of the contact portion of the finger, such that a direct current (DC) component of a pulse wave signal increases. By obtaining a relative magnitude of a contact load at each position of the contact surface based on such characteristic, the contact load processor 310 may obtain contact load distribution of the entire contact surface. In an example embodiment, a relative magnitude of a contact load at position ($x_1$, $y_1$) may be proportional to a division of the contact load at position (x$_1$, y$_1$) by a contact load distribution of an entire area including position (x$_1$, y$_1$).

For example, the contact load processor 310 may extract a DC component of a pulse wave signal at each position of the contact surface. In this case, the contact load processor 310 may extract the DC component by passing each pulse wave signal through a low-pass filter (LPF). The contact load processor 310 may obtain a relative magnitude of a contact load at each position based on the DC component of each pulse wave signal. For example, the contact load processor 310 may determine the extracted DC component value itself at each position, or a value calculated by applying a pre-defined function to the DC component value, to be the relative magnitude of a contact load.

Upon obtaining contact load distribution (i.e., the relative magnitude of the contact load at each position of the contact surface), the contact load processor 310 may obtain a second contact load at each position based on the relative magnitude of the contact load at each position and the first contact load detected by the load sensor 112.

For example, the contact load processor 310 may obtain the second contact load at each position of the contact surface by using the following Equation 1.

$$P(x, y) = P_r(x, y) \frac{K}{\sum P_r} \quad \text{[Equation 1]}$$

Herein, P(x, y) denotes the second contact load to be obtained at a position of (x, y) of the contact surface; P$_r$(x, y) denotes the relative magnitude of the contact load obtained by the contact load processor 310 at the position of (x, y) of the contact surface; K denotes an output value of the load sensor 112 that corresponds to the first contact load directed by the load sensor 112; and ΣPr denotes a total sum of contact load distributions obtained by the contact load processor 310 (i.e., a value obtained by adding together the relative magnitudes of the contact loads at the entire positions of the contact surface).

However, as illustrated in (2) of FIG. 2B, the contact load processor 310 may not detect a pulse wave signal at a specific position (e.g., at positions indicated by dotted lines) due to an arrangement of the pulse wave sensor array 111. In this case, the contact load processor 310 may estimate a DC component at a position, at which a pulse wave signal has not been detected, by performing interpolation based on the DC components of the detected pulse wave signal.

Upon obtaining the second contact load at each position of the contact surface, the contact load processor 310 may obtain a second contact load of a region of interest. For example, in the case where one position is included in a region of interest, the contact load processor 310 may obtain an actual contact load at that position as the second contact load of the region of interest. Alternatively, in the case where a plurality of positions are included in a region of interest, the contact load processor 310 may obtain at least one of a total sum of second contact loads at all the positions included in the region of interest, a mean value, a maximum value, a minimum value, a median value, and other statistical value thereof, and a value calculated using a pre-defined function, as the second contact load of the region of interest.

Upon obtaining the second contact load of the region of interest, the contact load processor 310 may obtain contact pressure by dividing the second contact load by an area of the region of interest. As the size of each pulse wave sensor is known and stored in apparatus 100a. 100b as a predetermined value, the area of the region of interest may be determined by the number of pulse wave sensors included in the region of interest.

The region of interest setter 340 may set at least one of the positions of the contact surface as a region of interest. For example, the region of interest setter 340 may set a predetermined region including a specific position of the contact surface (e.g., a center position of the contact surface) as a region of interest. In another example, once a pulse wave signal is detected at each position, the region of interest setter 340 may evaluate the quality of each pulse wave signal, and may set a region of interest based on the evaluation. In this case, the region of interest setter 340 may evaluate the quality of each pulse wave signal based on a maximum amplitude value of each pulse wave signal, a difference between a maximum amplitude value and a minimum amplitude value, an average amplitude value, the DC component of each pulse wave signal, and the like. However, the setting of the region of interest is not limited thereto, and the region of interest setter 340 may set a region of interest based on a position having the largest difference between a maximum amplitude value and a minimum amplitude value of the pulse wave signal, or a position having a maximum amplitude value, an average amplitude value, a DC component value greater than or equal to a threshold value, and the like.

Figure 4B:
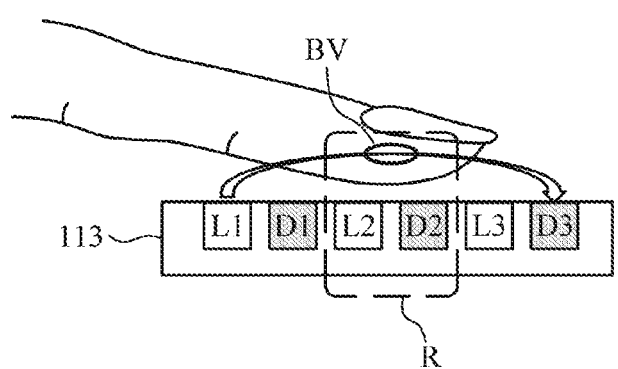

Referring to FIG. 4B, while an observation portion BV of a finger contacts a position of a pulse wave sensor L2 and D2 set as a region of interest R, when the finger presses the pulse wave sensor L2 and D2 with gradually increasing force, a second contact load of a region of interest R may be obtained based on the DC component of the pulse wave signal detected by the detector D2 of the region of interest R. Further, for example, a light source L1 and a detector D3 may be driven to detect a pulse wave signal of the observation portion BV as illustrated in FIG. 4B, and a pulse wave signal detected by the detector D3 may be used for estimating bio-information. For convenience of explanation, FIG. 4B illustrates an example where there is one pulse wave sensor L2 and D2 which contacts the observation portion BV, but the number of the pulse wave sensor is not limited thereto.

Figure 4C:
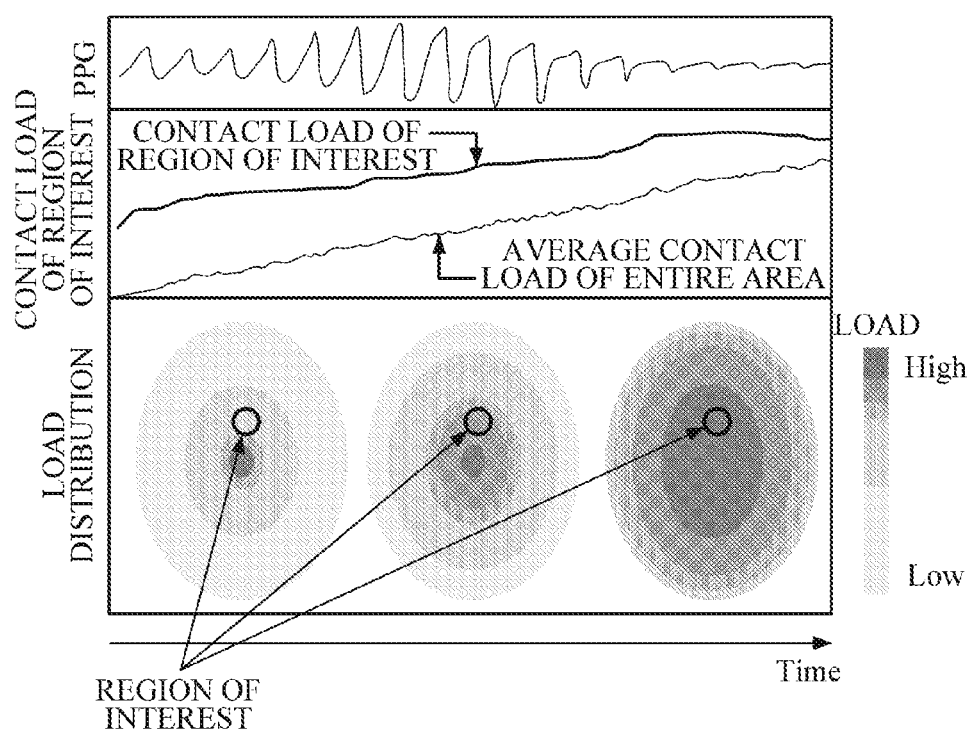

FIG. 4C illustrates, at the top labeled as "PPG", a pulse wave signal detected from a region of interest. In the middle of FIG. 4C labeled as "CONTACT LOAD OF REGION OF INTEREST," a change in an average contact load of the entire contact area and a change in the contact load of the region of interest are illustrated in a time domain. The region of interest may correspond to a certain point (x, y) in the entire contact area, or an area that is smaller than the entire contact area and located within the entire contact area. FIG. 4C shows a change in contact load distribution of the contact surface during a predetermined period of time, at the bottom labeled as "LOAD DISTRIBUTION." When a user presses the contact surface with an object (e.g., a finger of the user), the amount of pressure may vary depending on age, gender, characteristics of the object, and the like, such that contact pressure may not be measured accurately by using only an average value of the entire contact loads. In the embodiment, by setting an area, in which a contact state of an object is good, as a region of interest, and by obtaining contact pressure by using an actual contact load of the region of interest, bio-information may be estimated accurately regardless of a contact state.

Once the contact load processor 310 obtains the contact pressure, the feature value obtainer 320 may obtain feature values for estimating bio-information based on the pulse wave signal and the contact pressure. For example, referring to FIGS. 4D and 4E, the feature value obtainer 320 may obtain feature values for estimating blood pressure using oscillometry.

Figure 4D:
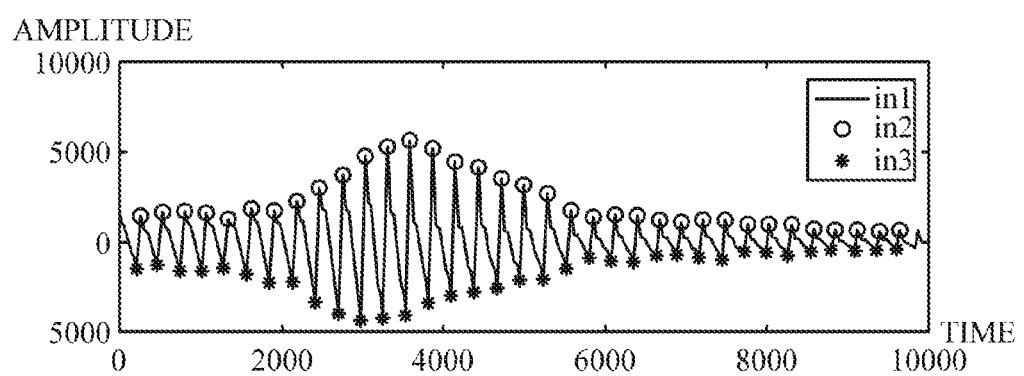

Referring to FIG. 4D, the feature value obtainer 320 may obtain an oscillometric envelope OW which represents a contact pressure versus pulse wave signal amplitude. The feature value obtainer 320 may extract a peak-to-peak point by subtracting an amplitude value in3 of a negative (−) point from an amplitude value in2 of a positive (+) point of a waveform envelope in1 at each measurement time of a pulse wave signal, and may obtain an oscillometric envelope OW by plotting a peak-to-peak amplitude at each measurement time based on a contact pressure value at the same measurement time as the peak-to-peak amplitude.

Figure 4E:
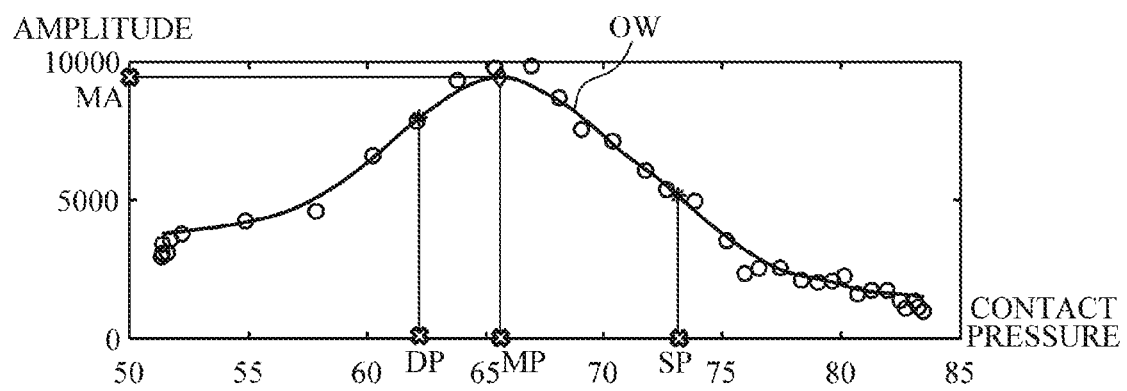

Referring to FIG. 4E, the feature value obtainer 320 may obtain feature values for estimating blood pressure from the obtained oscillometric envelope OW. The feature value obtainer 320 may obtain, as the feature values, an amplitude value MA and a contact pressure value MP of a maximum peak point, contact pressure values SP and DP located to the left and right of the contact pressure value MP of the maximum peak point and having a predetermined ratio (e.g., 0.5 to 0.7) to the contact pressure value MP, and the like.

In addition, the feature value obtainer 320 may select any pulse wave signal from among all the pulse wave signals obtained by the pulse wave sensor array 111, the pulse wave signal of the region of interest, and pulse wave signals of regions near the region of interest. For example, in the case where there is one pulse wave signal in the region of interest, the feature value obtainer 320 may select the pulse wave signal. Alternatively, the feature value obtainer 320 may select any pulse wave signal from among all the pulse wave signals or a plurality of pulse wave signals included in the region of interest, based on the quality of the pulse wave signals.

Further, the feature value obtainer 320 may select all the pulse wave signals or the plurality of pulse wave signals, and may obtain one pulse wave signal for extracting feature values by applying the plurality of pulse wave signals to a pre-defined combination model. Alternatively, in the case where the light source L1 and the detector D3 are predetermined for detecting a pulse wave signal from the observation portion BV as illustrated in FIG. 4B, the feature value obtainer 320 may select the pulse wave signal, detected by the detector D3, as a pulse wave signal for estimating bio-information. Moreover, the feature value obtainer 320 may obtain each oscillometric envelope OW based on the plurality of pulse wave signals and the contact pressure, and may combine feature values by applying various pre-defined functions to the feature values extracted from each oscillometric envelope OW. However, the selection of the pulse wave signal is not limited thereto.

The estimator 330 may estimate bio-information by combining the extracted feature values using a pre-defined bio-information estimation model. In particular, the bio-information estimation model may be defined as various linear or non-linear combination functions, such as addition, subtraction, division, multiplication, logarithmic value, regression equation, and the like, with no specific limitation. For example, the following Equation 2 represents a simple linear equation.

$$y = ax + b \quad \text{[Equation 2]}$$

Herein, y denotes a bio-information estimation value to be obtained; x denotes the extracted feature value; and a and b denote pre-calculated values obtained through preprocessing, and may be defined differently according to the types of bio-information to be obtained and user characteristics. For example, the estimator 330 may independently estimate mean arterial pressure (MAP), diastolic blood pressure (DBP), and systolic blood pressure (SBP) by using the above Equation 2 which is defined for each of the MAP, the DBP, and the SBP. For example, the estimator 330 may obtain the MAP, the DBP, and the SBP by inputting the extracted feature values MP, DP, and SP into a function defined for each of the values.

Upon receiving a request for estimating bio-information, the contact state guide part 350 may provide guide information on a reference contact pressure to be applied by a user to the sensor part 110. For example, the contact state guide part 350 may generate guide information including a reference contact pressure value at each measurement time and/or a change graph of the reference contact pressure during the entire measurement time period, and may output the generated guide information through an output interface which will be described later. The guide information may include information for inducing a user to press the sensor part 110 with gradually increasing force for a predetermined period of time when the user touches the sensor part 110 with an object; or information for inducing a user to press the sensor part 110 with gradually decreasing force when the user presses the sensor part 110 with a pressure greater than or equal to a threshold.

Further, once an actual contact pressure applied by a user to the sensor part 110 at each measurement time is obtained, the contact state guide part 350 may provide guide information on the actual contact pressure, so that the user may recognize a difference between the reference contact pressure and the contact pressure actually applied by the user. The contact state guide part 350 may generate a graph showing a change in the reference contact pressure and a change in the actual contact pressure, and may output the generated graph through an output interface, so that the user may visually recognize a difference between the reference contact pressure and the actual contact pressure.

In addition, the contact state guide part 350 may determine a contact state based on a pulse wave signal of a region of interest. In response to a pulse wave signal quality of a region of interest not satisfying pre-determined criteria, the contact state guide part 350 may determine that a contact state is not normal. For example, in the case where a difference between a maximum amplitude value and a minimum amplitude value of a pulse wave signal in a region of interest is smaller than or equal to a threshold, the contact state guide part 350 may determine that a contact state is not normal, and may guide a user to re-contact the sensor part 110. However, the determination of the contact state is not limited thereto.

Referring to FIG. 3B, the processor 300b according to an embodiment of the present disclosure includes a contact load processor 310, a feature value obtainer 320, an estimator 330, and a calibrator 360. The contact load processor 310, the feature value obtainer 320, and the estimator 330 are described above, such that detailed description thereof will be omitted.

Once a user contacts a contact surface of the sensor part 110 with a first object, the sensor part 110 may detect a first pulse wave signal at each position of the contact surface. In this case, the first object may include a reflecting panel RP made of a total reflection material. The reflecting panel RP may have a flat and even surface, and may be disposed on the sensor part 110 so that the user can touch the contact surface of the reflecting panel RP.

The calibrator 360 may generate a calibration model by using the first pulse wave signal detected at each position of the contact surface. For example, in the case where the reflecting panel RP made of a total reflection material allows a contact load to uniformly act on the sensor part 110, values output by each detector of the pulse wave sensor array 111 should be equal to each other. However, if the values output by each detector are different from each other, accuracy in estimating bio-information may be reduced. In order to prevent the occurrence of degradation in accuracy, the calibrator 360 may generate a calibration model for calibrating a difference between the values output by each detector to 0. The following Equation 3 shows an example of a calibration model, but the calibration model is not limited thereto.

$$F_{ic} = \alpha F_{im} + \beta \qquad \text{[Equation 3]}$$

Herein, $F_{im}$ and $F_{ic}$ each denotes a value output by a detector i and a value obtained after calibration; and $\alpha$ and $\beta$ denote values determined by the calibrator 360.

Once a second pulse wave signal at each position is detected from a second object, the calibrator 360 may calibrate the second pulse wave signal by using the generated calibration model. That is, the calibrator 360 may calibrate the values detected by the detector at each position by using the calibration model. In this case, the second object may be a human body tissue such as a finger, a wrist, and the like, but is not limited thereto.

The contact load processor 310 may obtain contact load distribution (i.e., a relative magnitude of a contact load at each position) based on a DC component of the calibrated second pulse wave signal.

The feature value obtainer 320 and the estimator 330 may estimate bio-information using the obtained contact load distribution and the calibrated second pulse wave signal, as described above.

The calibrator 360 may perform calibration for the first time at the time of manufacturing the apparatuses 100a and 100b for estimating bio-information at the request of a manufacturer, and may perform calibration later in response to a request of a user. Further, the calibrator 360 may determine whether calibration is required at predetermined calibration intervals or based on an estimation result of bio-information. For example, the calibrator 360 may determine whether to perform calibration by combining various conditions, such as a total number of times estimated blood pressure values fall outside a predetermined reference range, a number of times the estimated blood pressure values continuously fall outside the range, and a case where a change from the reference blood pressure shows a continuous increasing or decreasing trend. However, the determination on calibration is not limited thereto. Upon determining that calibration is required, the calibrator 360 may guide a user to perform calibration.

Referring back to FIG. 1B, the apparatus for estimating bio-information 100b may further include an output interface 130, a memory 140, and a communication interface 150.

The output interface 130 may output results processed by the sensor part 110 and the processor 120. For example, the output interface 130 may visually output an estimated bio-information value and/or guide information by using a display module, or may output the information in a non-visual manner through voice, vibrations, tactile sensation, and the like by using a speaker module, a haptic module, and the like. The output interface 130 may divide a display area into two or more areas according to a setting, in which the output interface 130 may output the pulse wave signal, the contact force, the contact area, and the like, which are used for estimating bio-information, in various forms of graphs in a first area; and may output an estimated bio-information value in a second area. In this case, if an estimated bio-information value falls outside a normal range, the output interface 130 may output warning information in various manners, such as highlighting an abnormal value in red and the like, displaying the abnormal value along with a normal range, outputting a voice warning message, adjusting a vibration intensity, and the like.

The memory 140 may store processing results of the sensor part 110 and the processor 120. Further, the memory 140 may store various criteria required for estimating bio-information. For example, the criteria may include user feature information such as a user's age, gender, health condition, and the like. In addition, the criteria may include various types of information, such as a bio-information estimation model, bio-information estimation criteria, a reference contact pressure, calibration criteria, and the like, but are not limited thereto.

In this case, the memory 140 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 150 may communicate with an external device 170 by using wired or wireless communication techniques under the control of the processor 120, and may transmit and receive various data to and from the external device 170. For example, the communication interface 150 may transmit an estimation result of bio-information to the external device 170, and may receive various criteria required for estimating bio-information from the external device 170. In this case, examples of the external device 170 may include a cuff-type blood pressure measuring device, and an information processing device such as a smartphone, a tablet PC, a desktop computer, a laptop computer, and the like.

Examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

Figure 5:
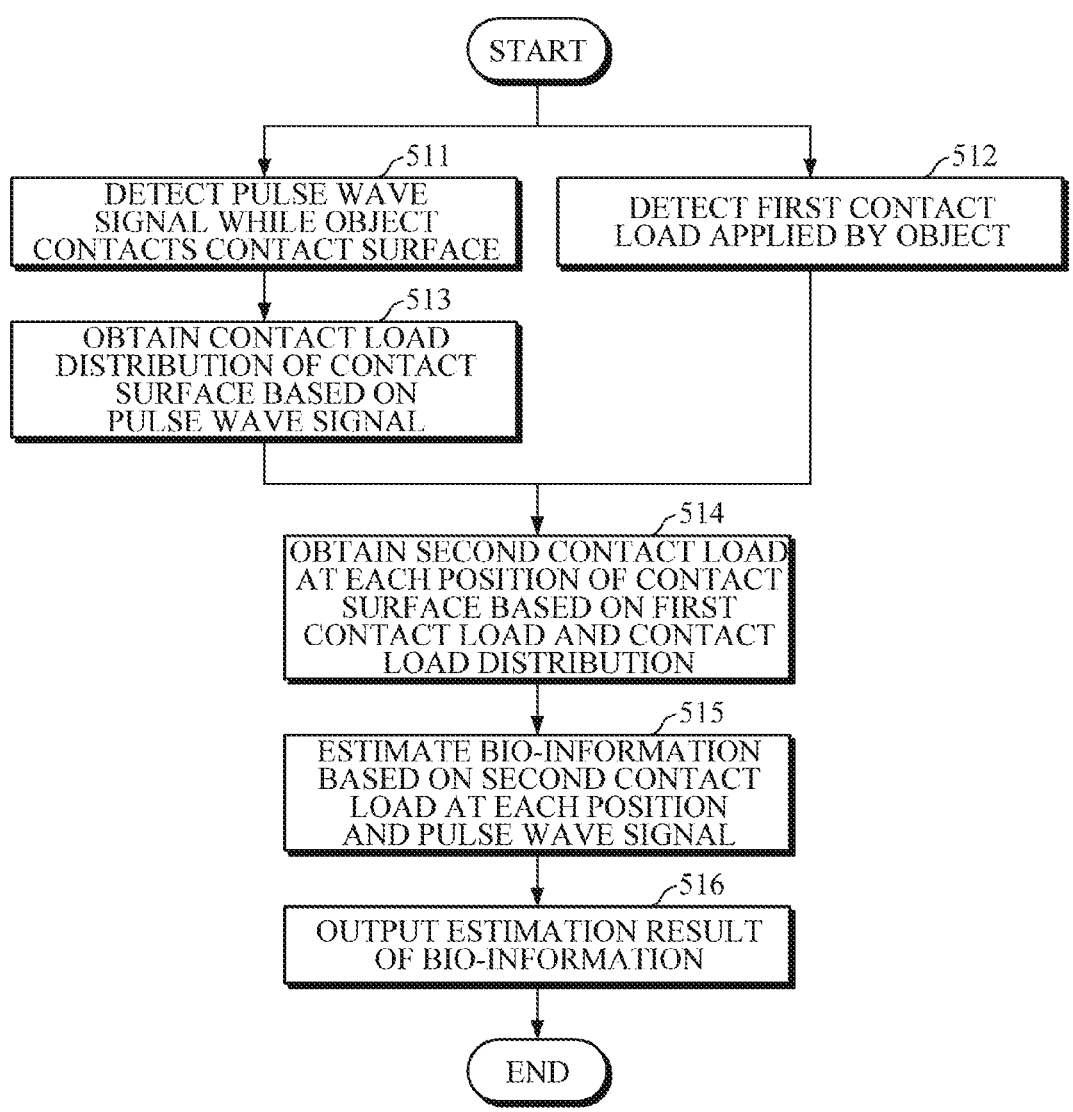
FIG. 5 is a flowchart illustrating a method of estimating bio-information according to an embodiment.

FIG. 5 is a flowchart illustrating a method of estimating bio-information according to an embodiment of the present disclosure. The method of estimating bio-information of FIG. 5 may be an example of a method of estimating bio-information performed by the apparatuses 100a and 100b for estimating bio-information, which will be briefly described below in order to avoid redundancy.

While an object contacts a sensor part, the apparatus for estimating bio-information may detect a pulse wave signal, and a first contact load applied by the object to the sensor part in operations 511 and 512. Once a user contacts a contact surface with the object for estimating bio-information, the apparatus for estimating bio-information may provide guide information on a reference contact pressure to be applied by the object to the contact surface.

Then, the apparatus for estimating bio-information may obtain contact load distribution of the contact surface based on the detected pulse wave signal in operation 513. For example, as described above, the apparatus for estimating bio-information may extract a DC component of the pulse wave signal detected at each position of the contact surface, and may obtain a relative magnitude of the contact load at each position by using the extracted DC component value. In this case, the apparatus for estimating bio-information may determine the extracted DC component value itself at each position, or a value calculated by applying a predefined function to the DC component value at each position, to be the relative magnitude of a contact load at each position of the contact surface.

Subsequently, the apparatus for estimating bio-information may obtain a second contact load at each position of the contact surface in operation 514 based on the first contact load detected in operation 512 and the contact load distribution obtained in operation 513. In this case, the apparatus for estimating bio-information may set a region of interest on the contact surface, and may obtain a second contact load of the set region of interest. For example, the apparatus for estimating bio-information may set a region of interest based on a center position of the contact surface. In this case, along with the guide information on the reference contact pressure in operation 511, the apparatus for estimating bio-information may guide a user to place an observation portion of an object, e.g., a fingerprint center point of a finger, on a region of interest (e.g., a center position of the contact surface). In another example, a position of contact of the fingerprint center point of a finger with the contact surface may vary depending on characteristics of a finger of each user, or habit of contact of each user. By considering characteristics of each user, the apparatus for estimating bio-information may set a region of interest for each user based on the position of contact of the fingerprint center point with the contact surface. Alternatively, the apparatus for estimating bio-information may set one or more positions as a region of interest based on the quality of the pulse wave signal detected at each position of the contact surface.

Next, the apparatus for estimating bio-information may estimate bio-information in operation 515 by using the second contact load at each position of the contact surface and the pulse wave signal detected in operation 511. For example, the apparatus for estimating bio-information may obtain contact pressure based on the second contact load of the region of interest and an area of the region of interest, and may estimate blood pressure by using oscillometry based on the contact pressure and the pulse wave signal.

Then, the apparatus for estimating bio-information may output an estimation result of bio-information in operation 516. In this case, the apparatus for estimating bio-information may output the estimation result of bio-information using various output devices, such as a display module for visual output, a speaker module for voice output, a haptic module for tactile output through vibrations, tactile sensation, and the like.

Figure 6:
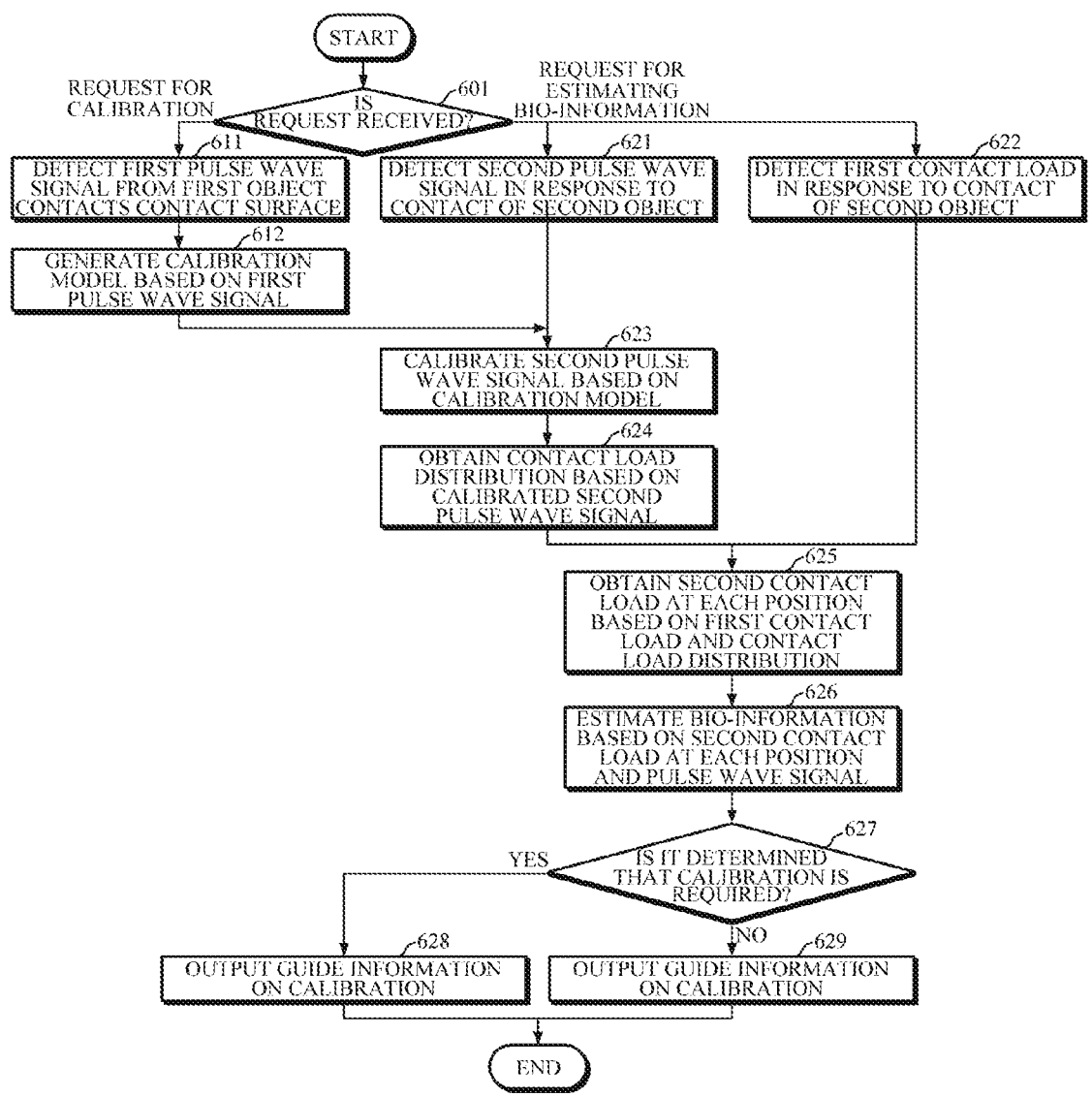
FIG. 6 is a flowchart illustrating a method of estimating bio-information according to another embodiment.

FIG. 6 is a flowchart illustrating a method of estimating bio-information according to another embodiment of the present disclosure. The method of estimating bio-information of FIG. 6 may be an example of a method of estimating bio-information performed by the apparatuses 100a and 100b for estimating bio-information, which will be briefly described below in order to avoid redundancy.

Upon receiving a request from a user, the apparatus for estimating bio-information may determine whether the request is a request for calibration or a request for estimating bio-information in operation 601. The user may perform calibration according to guide information on calibration provided by the apparatus for estimating bio-information or according to their own determination. The calibration may be performed for the first time at the time of manufacturing the apparatus for estimating bio-information in response to a request of a manufacturer.

Then, upon determining in operation 601 that the user's request is a request for calibration, the apparatus for estimating bio-information may detect a first pulse wave signal from a first object while the first object contacts a contact surface in operation 611. In this case, the first object may be a reflecting panel RP which allows contact pressure to be uniformly applied to the contact surface. Upon requesting calibration and contacting the first object with the contact surface, the user may change the contact pressure by pressing the first object with a finger and the like with gradually increasing force. In this case, the apparatus for estimating bio-information may guide change in a reference contact pressure to be applied for a predetermined period of time. Each pulse wave sensor of the pulse wave sensor array 111 may drive light sources with the same wavelength and current intensity.

Subsequently, the apparatus for estimating bio-information may generate a calibration model based on the detected first pulse wave signal in operation 612. For example, while contact pressure is applied uniformly to all positions of the contact surface using the reflecting panel RP, the apparatus for estimating bio-information may drive light sources with the same driving current, and may generate a calibration model for calibrating values, output by the detector at each position, to an equal value. The generated calibration model is stored in the memory, and may be used for estimating bio-information.

Upon determining in operation 601 that the user's request is a request for estimating bio-information, the apparatus for estimating bio-information may detect a second pulse wave signal and a first contact load in response to contact of a second object in operations 621 and 622. In this case, the second object may be a human skin tissue such as a finger or a wrist; and each light source driving current of each pulse wave sensor may be the same light source driving current when calibration is performed.

Then, upon obtaining the second pulse wave signal at each position of the contact surface, the apparatus for estimating bio-information may calibrate the second pulse wave signal using the calibration model in operation 623, and may obtain contact load distribution based on the calibrated second pulse wave signal in operation 624.

Subsequently, the apparatus for estimating bio-information may obtain a second contact load at each position in operation 625 based on the contact load distribution and the first contact load detected in operation 622, and may estimate bio-information based on the obtained second contact load and the pulse wave signal in operation 626. In this case, the apparatus for estimating bio-information may obtain contact pressure based on a second contact load and an area of a region of interest, and may estimate bio-information using oscillometry based on the contact pressure and the pulse wave signal.

Next, the apparatus for estimating bio-information may determine whether calibration is required based on the estimation result of bio-information in operation 627. For example, the apparatus for estimating bio-information may determine that calibration is required in cases where an estimated blood pressure value falls outside a predetermined normal range, a total number of times the estimated values fall outside the normal range exceeds a threshold, a number of times the estimated blood pressure values continuously fall outside the range is greater than or equal to a predetermined number of times, a difference between an estimated blood pressure value and a reference blood pressure value is greater than or equal to a threshold, a change in the estimated blood pressure compared to the reference blood pressure shows a continuous increasing or decreasing trend. However, the determination on calibration is not limited to the above cases.

Then, upon determining in operation 627 that calibration is required, the apparatus for estimating bio-information may output guide information on calibration, e.g., information for inducing calibration, information on procedures required for calibration, and the like, in operation 628. Upon determining in operation 627 that calibration is not required, or even when calibration is required, the apparatus for estimating bio-information may output an estimation result of bio-information according to a setting in operation 629.

Figure 7:
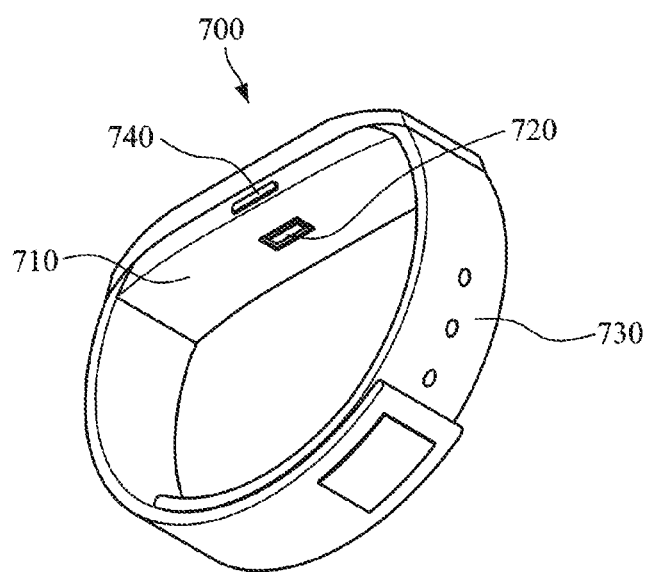
FIG. 7 is a diagram illustrating a wearable device, to which an apparatus for estimating bio-information is applied.

FIG. 7 is a diagram illustrating a wearable device, to which various embodiments of an apparatus for estimating bio-information are applied. Various embodiments of the above-described apparatus for estimating bio-information may be mounted in a smart watch worn on a wrist or a smart band-type wearable device. However, the wearable device is merely an example for convenience of explanation, and it should not be construed that application of the embodiments is limited to a smart watch or a smart band-type wearable device.

Referring to FIG. 7, the wearable device 700 includes a main body 710 and a strap 730.

The strap 730 may be flexible, and may be connected to both ends of the main body 710 to be bent around a user's wrist or may be bent in a manner which allows the strap 730 to be detached from a user's wrist. Alternatively, the strap 730 may be formed as a band that is not detachable. In this case, air may be injected into the strap 730 or an airbag may be included in the strap 730, so that the strap 730 may have elasticity according to a change in pressure applied to the wrist, and the change in pressure of the wrist may be transmitted to the main body 710.

A battery, which supplies power to the wearable device 700, may be embedded in the main body 710 or the strap 730.

Further, the main body 710 includes a sensor part 720 mounted on one side thereof. The sensor part 720 may be composed of a pulse wave sensor array 111 and a load sensor 112, as described above. When a user changes contact pressure between the wrist and the sensor part 720 for a predetermined period of time, the sensor part 720 detects a contact load applied by the wrist, and may detect a pulse wave signal from the blood vessel tissue of the wrist.

For example, a user may change contact pressure between the wrist and the sensor part 720 by touching a display, mounted on a front surface of the main body 710, with gradually increasing force with a finger of the other hand while wearing the main body 710, or by changing a thickness of the wrist by making hand movements, e.g., slowly opening the hand after clenching the fist while wearing the main body 710 on the wrist. In this case, the change in the thickness of the wrist leads to a change in tension of the strap wrapped around the wrist, thereby causing a change in contact pressure between the wrist and the sensor part 720.

Further, the main body 710 may include a processor which estimates bio-information by processing the pulse wave signal and the contact load which are detected by the sensor part 720. In response to a user's request for estimating bio-information, the processor may generate a control signal to control the sensor part 720. Once the pulse wave signal at each position of the contact surface is detected, the processor may obtain contact load distribution by using the DC component of the pulse wave signal. Further, the processor may obtain an actual contact load at each position by using the obtained contact load distribution and the contact load detected by the sensor part 720, and may estimate bio-information by using the actual contact load. For example, the processor may calculate contact pressure based on the actual contact load and the area of the region of interest, and may estimate blood pressure using socillometry based on the calculated contact pressure and the pulse wave signal.

Upon receiving the request for estimating bio-information from a user, the processor may provide guide information on a contact state to a user through a display, so that the user may apply pressure to the main body 710 to change contact pressure between the sensor part 720 and the object. In this case, the display may be mounted on a front surface of the main body 710, and may visually output guide information on a contact state and/or an estimation result of bio-information.

A memory may be mounted in the main body 710, and may store various types of information processed by the processor, and various criteria for estimating bio-information.

Further, the wearable device 700 may include a manipulator 740 which receives a control command of a user and transmits the received control command to the processor. The manipulator 740 may be mounted on a side surface of the main body 710, and may include a function for inputting a command to turn on/off the wearable device 700.

Moreover, the wearable device 700 may include a communication interface for transmitting and receiving various data to and from an external device, and various other modules for performing additional functions provided by the wearable device 700.

Figure 8:
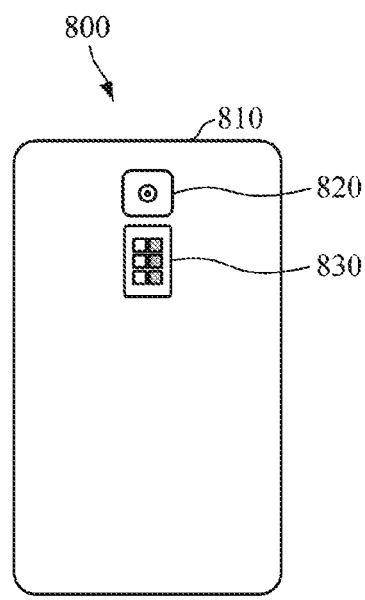
FIG. 8 is a diagram illustrating a smart device, to which an apparatus for estimating bio-information is applied.

FIG. 8 is a diagram illustrating a smart device, to which embodiments of an apparatus for estimating bio-information are applied. In this case, the smart device may be a smartphone, a tablet PC, and the like.

Referring to FIG. 8, the smart device 800 includes a main body 810 and a sensor part 830 mounted on one surface of the main body 810. The sensor part 830 may include a pulse wave sensor array 111, including a light source array and a detector array, and a load sensor 112. The sensor part 830 may be mounted on a rear surface of the main body 810, but is not limited thereto, and may be configured in combination with a fingerprint sensor or a touch panel formed on the front surface of the main body 810.

In addition, a display may be mounted on a front surface of the main body 810. The display may visually display an estimation result of bio-information and the like. The display may include a touch panel, and may receive various types of information input through the touch panel and transmit the received information to the processor.

Moreover, an image sensor 820 may be mounted in the main body 810. When a user's finger approaches the sensor part 830 to measure a pulse wave signal, the image sensor 820 may capture an image of the finger and may transmit the captured image to the processor. In this case, based on the image of the finger, the processor may identify a relative position of the finger with respect to an actual position of the sensor part 830, and may provide the relative position of the finger to the user through the display, so that pulse wave signals may be measured with improved accuracy.

Various other modules for performing many embodiments of the aforementioned apparatus for estimating bio-information may be mounted in the smart device 800, and detailed description thereof will be omitted.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating bio-information, the apparatus comprising:
    a sensor part comprising:
        a pulse wave sensor array configured to detect a pulse wave signal when an object contacts a contact surface of the sensor part; and
        a load sensor configured to detect a first contact load applied by the object to the contact surface; and
    a processor configured to obtain contact load distribution of the contact surface based on the pulse wave signal, obtain a second contact load at each position of the contact surface based on the contact load distribution and the first contact load, and estimate bio-information based on the second contact load and the pulse wave signal.

2. The apparatus of claim 1, wherein the pulse wave sensor array comprises:
    a light source array configured to emit light onto the object; and
    a detector array configured to detect light reflected or scattered from the object.

3. The apparatus of claim 2, wherein the sensor part further comprises a substrate on which the pulse wave sensor array is formed in a predetermined pattern, by using at least one of wire bonding, flip-chip bonding, and a microfabrication technique.

4. The apparatus of claim 3, wherein:
    the light source array is arranged on the substrate by at least one of the wire bonding and the flip-chip bonding; and
    the detector array is patterned on the substrate by the microfabrication technique.

5. The apparatus of claim 1, wherein the sensor part further comprises a touch sensor disposed on the pulse wave sensor array to be contacted by the object.

6. The apparatus of claim 1, wherein the processor is further configured to extract each direct current (DC) component from the pulse wave signal detected by the pulse wave sensor array at each position of the contact surface, and obtain a relative magnitude of the second contact load at each position based on the extracted each DC component.

7. The apparatus of claim 6, wherein the processor is further configured to perform interpolation on the extracted each DC component to estimate the DC component at a specific position of the contact surface, in response to the pulse wave signal not being detected from the specific position of the contact surface.

8. The apparatus of claim 6, wherein the processor is further configured to obtain the second contact load at each position by multiplying a value, obtained by dividing the first contact load by a total sum of the contact load distributions, by the relative magnitude of the contact load at each position.

9. The apparatus of claim 1, wherein the processor is further configured to obtain a contact pressure between the object and the sensor part based on the second contact load of a region of interest and an area of the region of interest, and estimate the bio-information based on the contact pressure and the pulse wave signal.

10. The apparatus of claim 9, wherein the processor is further configured to set the region of interest based on at least one of a blood vessel distribution of the object, an arrangement of the pulse wave sensor array, a specific position of the contact surface, and the second contact load at each position of the contact surface.

11. The apparatus of claim 9, wherein the processor is further configured to obtain an oscillometric envelope which represents a contact pressure versus pulse wave signal amplitude at each measurement time, and estimate the bio-information based on the oscillometric envelope.

12. The apparatus of claim 11, wherein the processor is further configured to estimate the bio-information based on a feature value of the oscillometric envelope, and
    the feature value comprises one or more of a contact pressure value of a maximum amplitude point, a first contact pressure value that is less than the contact pressure value of the maximum amplitude point and having a first predetermined ratio to the maximum amplitude point, and a second contact pressure value that is greater than the contact pressure value of the maximum amplitude point and having a second predetermined ratio to the maximum amplitude point.

13. The apparatus of claim 1, further comprising an output interface, which in response to a request for estimating bio-information, outputs guide information on contact pressure between the object and the sensor part.

14. The apparatus of claim 1, wherein the processor is further configured to obtain a contact pressure of a region of interest based on the second contact load of the region of interest and an area of the region of interest, and determine a contact state between the object and the sensor part based on the contact pressure.

15. The apparatus of claim 1, wherein the bio-information comprises one or more of blood pressure, vascular age, arterial stiffness, aortic pressure waveform, vascular compliance, stress index, degree of fatigue, skin elasticity, and skin age.

16. A method of estimating bio-information, the method comprising:
  detecting a pulse wave signal when an object contacts a contact surface of a sensor;
  detecting a first contact load applied by the object to the contact surface;
  obtaining contact load distribution of the contact surface based on the pulse wave signal;
  obtaining a second contact load at each position of the contact surface based on the contact load distribution and the first contact load; and
  estimating bio-information based on the second contact load and the pulse wave signal.

17. The method of claim 16, wherein the obtaining the contact load distribution comprises:
  extracting each direct current (DC) component from the pulse wave signal at each position of the contact surface; and
  obtaining a relative magnitude of the first contact load at each position based on the extracted each DC component.

18. The method of claim 17, wherein the obtaining the contact load distribution comprises, performing interpolation on the extracted each DC component to estimate the DC component at a specific position of the contact surface, in response to the pulse wave signal not being detected from the specific position of the contact surface.

19. The method of claim 16, wherein the estimating the bio-information comprises setting a region of interest based on at least one of a blood vessel distribution of the object, an arrangement of a pulse wave sensor array that detects the pulse wave signal, a specific position of the contact surface of the sensor, and the second contact load at each position of the contact surface.

20. The method of claim 16, wherein the estimating the bio-information further comprises obtaining a contact pressure between the object and the sensor based on the second contact load of a region of interest and an area of the region of interest.

21. The method of claim 20, wherein the estimating the bio-information comprises obtaining an oscillometric envelope which represents a contact pressure versus pulse wave signal amplitude at each measurement time, and estimating bio-information based on the oscillometric envelope.

22. An apparatus for estimating bio-information, the apparatus comprising:
  a sensor part comprising a pulse wave sensor array configured to detect a pulse wave signal when an object contacts a contact surface of the sensor part, and a load sensor configured to detect a first contact load applied by the object to the contact surface;
  a memory configured to store a calibration model based on a reference pulse wave signal detected from a reference object; and
  a processor configured to:
    retrieve the calibration model from the memory;
    calibrate the pulse wave signal detected by the pulse wave sensor array, based on the calibration model;
    obtain a second contact load at each position of the contact surface based on the calibrated pulse wave signal and the first contact load; and
    estimate bio-information based on the second contact load and the calibrated pulse wave signal.

23. The apparatus of claim 22, wherein the reference object comprises a reflecting panel that is made of a total reflection material and has a flat surface.

24. The apparatus of claim 22, wherein the processor is further configured to generate the calibration model to calibrate a difference between output values of the pulse wave sensor array at each position of the contact surface, to 0, and store the calibration model in the memory.

25. The apparatus of claim 22, wherein the processor is further configured to obtain a contact pressure based on the second contact load of a region of interest and an area of the region of interest, and estimate the bio-information based on the contact pressure and the calibrated pulse wave signal.

26. The apparatus of claim 22, wherein the object is a user of the apparatus, and
  wherein the processor is further configured to determine whether to perform an additional calibration based on a result of estimating the bio-information based on the second contact load and the calibrated pulse wave signal, and provide guide information on the additional calibration to the user.

* * * * *